United States Patent
Yamamoto et al.

(10) Patent No.: US 7,588,172 B2
(45) Date of Patent: Sep. 15, 2009

(54) LIQUID SPRAY TOOL FOR ENDOSCOPE

(75) Inventors: Akira Yamamoto, Tokyo (JP); Tetsuya Nakamura, Saitama (JP); Yae Kurosawa, Kanagawa (JP); Yusuke Iimori, Tokyo (JP); Pilryon Lee, Kanagawa (JP)

(73) Assignee: Hoya Corporation, Tokyo (JP)

( * ) Notice: Subject to any disclaimer, the term of this patent is extended or adjusted under 35 U.S.C. 154(b) by 480 days.

(21) Appl. No.: 11/611,245

(22) Filed: Dec. 15, 2006

(65) Prior Publication Data

US 2007/0138206 A1 Jun. 21, 2007

(30) Foreign Application Priority Data

Dec. 19, 2005 (JP) ............................ P2005-364521

(51) Int. Cl.
*B67D 5/38* (2006.01)
(52) U.S. Cl. ................... 222/158; 222/207; 600/156
(58) Field of Classification Search ......... 222/155–159, 222/633, 213, 214, 133, 134, 202, 203, 207, 222/209, 212; 600/104, 156, 158, 159, 169; 606/20–22; 604/265–267; 239/366–369; 141/23–26, 31, 313
See application file for complete search history.

(56) References Cited

U.S. PATENT DOCUMENTS

| | | | | |
|---|---|---|---|---|
| 3,750,914 | A * | 8/1973 | Patel ........................... | 222/543 |
| 5,403,309 | A * | 4/1995 | Coleman et al. .............. | 606/20 |
| 5,497,944 | A | 3/1996 | Weston et al. | |
| 6,264,636 | B1 * | 7/2001 | Holm et al. .................. | 604/183 |
| 6,354,519 | B1 | 3/2002 | Kidooka et al. | |
| 6,383,181 | B1 * | 5/2002 | Johnston et al. .............. | 606/24 |
| 6,425,535 | B1 * | 7/2002 | Akiba ........................ | 239/369 |
| 6,454,790 | B1 * | 9/2002 | Neuberger et al. ............ | 607/88 |
| 6,702,738 | B2 * | 3/2004 | Ito ............................. | 600/158 |
| 6,786,865 | B2 * | 9/2004 | Dhindsa ...................... | 600/159 |

(Continued)

FOREIGN PATENT DOCUMENTS

JP 5-509241 12/1993

(Continued)

OTHER PUBLICATIONS

English Language Abstract of JP 2001-104489.

(Continued)

*Primary Examiner*—Lien T Ngo
(74) *Attorney, Agent, or Firm*—Greenblum & Bernstein, P.L.C.

(57) ABSTRACT

A liquid spray tool for an endoscope includes a flexible tube to be inserted into and extracted from a treatment tool insertion channel of the endoscope, a liquid storage pouch configured to pool solution to be conveyed into the flexible tube therein, a liquid measuring pouch for measuring an amount of the solution which is arranged between a rear end of the flexible tube and a distal end of the liquid storage pouch, and a first one-way valve arranged between the liquid storage pouch and the liquid measuring pouch, the first one-way valve being configured to allow the solution to pass theretrough from an inside of the liquid storage pouch to an inside of the liquid measuring pouch, and to prevent the solution from passing theretrough from the inside of the liquid measuring pouch to the inside of the liquid storage pouch.

18 Claims, 6 Drawing Sheets

U.S. PATENT DOCUMENTS

| | | | |
|---|---|---|---|
| 6,840,902 B2 * | 1/2005 | Sano et al. | 600/158 |
| 2003/0032862 A1 | 2/2003 | Ota et al. | |
| 2003/0043264 A1 | 3/2003 | Furuya et al. | |
| 2003/0045779 A1 | 3/2003 | Ito | |
| 2006/0052663 A1 * | 3/2006 | Koitabashi | 600/132 |
| 2006/0281973 A1 | 12/2006 | Sugita | |

FOREIGN PATENT DOCUMENTS

| | | |
|---|---|---|
| JP | 6-070986 | 3/1994 |
| JP | 2001-104489 | 4/2001 |
| JP | 2001-104490 | 4/2001 |
| JP | 2001-137349 | 5/2001 |
| JP | 2001-340464 | 12/2001 |

OTHER PUBLICATIONS

English Language Abstract of JP 2001-104490.
English Language Abstract of JP 2001-340464.
English Language Abstract of JP 6-070986.
U.S. Appl. No. 11/610,081 to Yamamoto et al., filed Dec. 13, 2006.

* cited by examiner

LIQUID SPRAY TOOL FOR ENDOSCOPE

BACKGROUND OF THE INVENTION

The present invention relates to a liquid spray tool for an endoscope that is used to spray solution in a human body with being inserted into a treatment tool insertion channel of the endoscope.

In an endoscope observation, it is possible, in some cases, to identify a condition of lesion that cannot be clarified in a usual endoscope observation by applying dye solution to in vivo mucous membrane. In the case of spraying such solution in a human body, a liquid spraying tool for the endoscope, configured as a flexible tube to be inserted into and extracted from a treatment tool insertion channel of the endoscope, is employed (for example, see Japanese Patent Provisional Publications No. 2001-104490 and No. 2001-137349).

Any of conventional liquid spray tools for the endoscope as aforementioned is used with a glass syringe that pools the solution therein being connected with a liquid injection pipe sleeve, as an injection needle pipe sleeve, which is attached to a rear end portion of the flexible tube configured to be inserted into and extracted from the treatment tool insertion channel of the endoscope.

However, in an operation of attaching the glass syringe to the liquid injection pipe sleeve or injecting the solution from the glass syringe to the liquid injection pipe sleeve in a dim endoscope examination room, it sometimes causes a problem that the solution, which leaks from a connection part between the liquid injection pipe sleeve and the glass syringe due to an imperfect connection therebetween or a too strong force for holding the pipe sleeve in an operation of injecting the solution, dirties an operator's hand and/or a surrounding area.

SUMMARY OF THE INVENTION

The present invention is advantageous in that there can be provided an improved liquid spray tool for an endoscope that is configured to smoothly spray an appropriate amount of solution in a human body without solution leak that causes a dirtied operator's hand and/or a dirtied surrounding area at an operator's hand side.

According to an aspect of the present invention, there is provided a liquid spray tool for an endoscope configured to spray solution to in vivo tissue, which includes: a flexible tube to be inserted into and extracted from a treatment tool insertion channel of the endoscope; a liquid storage pouch configured to pool the solution to be conveyed into the flexible tube therein; a liquid measuring pouch for measuring an amount of the solution to be conveyed into the flexible tube, the liquid measuring pouch being arranged between a rear end of the flexible tube and a distal end of the liquid storage pouch; and a first one-way valve arranged between the liquid storage pouch and the liquid measuring pouch, the first one-way valve being configured to allow the solution to pass theretrough from an inside of the liquid storage pouch to an inside of the liquid measuring pouch, and to prevent the solution from passing theretrough from the inside of the liquid measuring pouch to the inside of the liquid storage pouch.

Optionally, the liquid measuring pouch may be configured to have a volume smaller than that of the liquid storage pouch.

Optionally, the liquid storage pouch may be formed from opaque material.

Optionally, the first one-way valve may be formed with the distal end of the liquid storage pouch being narrowed.

Optionally, the liquid measuring pouch may include a scale for measuring an amount of the solution pooled therein.

Optionally, all of outer surface portions of the liquid spray tool, including a distal end of the flexible tube, may be sealed against an outside of the liquid spray tool.

Still optionally, the distal end of the flexible tube may be sealed by welding.

Alternatively or optionally, the liquid spray tool may further include a stopple for sealing a distal end of the flexible tube.

Optionally, the liquid spray tool may further include a second one-way valve configured to allow air to pass therethrough from an outside to an inside of the liquid storage pouch into the liquid storage pouch, and to prevent the solution from passing therethrough from the inside to the outside of the liquid storage pouch.

Optionally, the liquid storage pouch may be formed from resilient material.

Yet optionally, the liquid storage pouch may be formed from silicon rubber.

Optionally, the liquid measuring pouch may be formed from transparent resilient material.

Further optionally, the liquid measuring pouch may be formed from silicon rubber.

Optionally, the flexible tube may be formed from the same material as at least one of the liquid storage pouch and liquid measuring pouch.

Optionally, the flexible tube may be formed from silicon rubber.

Alternatively or optionally, the flexible tube is formed from material of a stiffness higher than silicon rubber.

Still optionally, the flexible tube may be formed from silicon resin.

Optionally, the flexible tube may be formed from fluorocarbon resin.

BRIEF DESCRIPTION OF THE ACCOMPANYING DRAWINGS

DETAILED DESCRIPTION OF THE EMBODIMENTS

Figure 4:
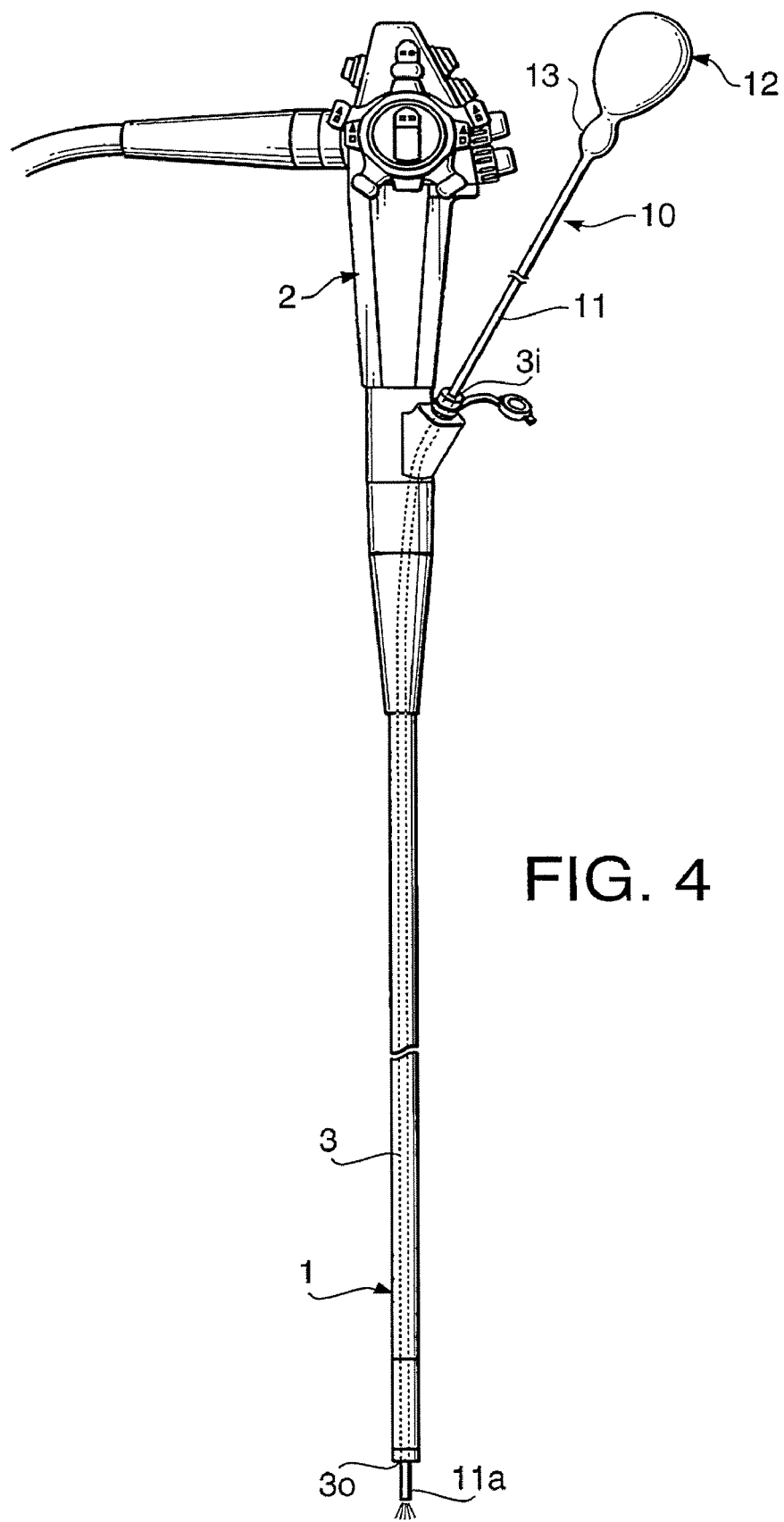
FIG. 4 is an external view of the liquid spray tool for the endoscope in use with being inserted into a treatment tool insertion channel of the endoscope according to the first embodiment of the present invention.

Hereinafter, embodiments according to the present invention will be explained with reference to the accompanying drawings. FIG. 4 shows a state where a liquid spray tool 10 for an endoscope according to the present invention is used. In FIG. 4, a reference sign 1 denotes an insertion part, and a reference sign 2 denotes an operating part. A liquid spray tool 10 is used with being inserted into a treatment tool insertion channel 3 provided over a whole length of the insertion part 1 of the endoscope. After use of the liquid applicator 10, it is extracted from the treatment tool insertion channel 3.

A flexible tube 11 that constitutes the liquid spray tool 10 is formed longer than the treatment tool insertion channel 3 by one meter. A distal end 11a of the flexible tube is protruded forward from a treatment tool protrusion opening 3o at a distal end of the treatment tool insertion channel 3.

To a rear end of the flexible tube 11 extending from a treatment tool insertion opening 3i of the endoscope to an operator's hand side, there is connected via a liquid measuring pouch 13 a liquid storage pouch 12 which is previously filled with solution to be conveyed into the flexible tube 11. The liquid spray tool 10 according to the present invention is formed integrally with the flexible tube 11, liquid storage pouch 12, and liquid measuring pouch 13.

Figure 1:
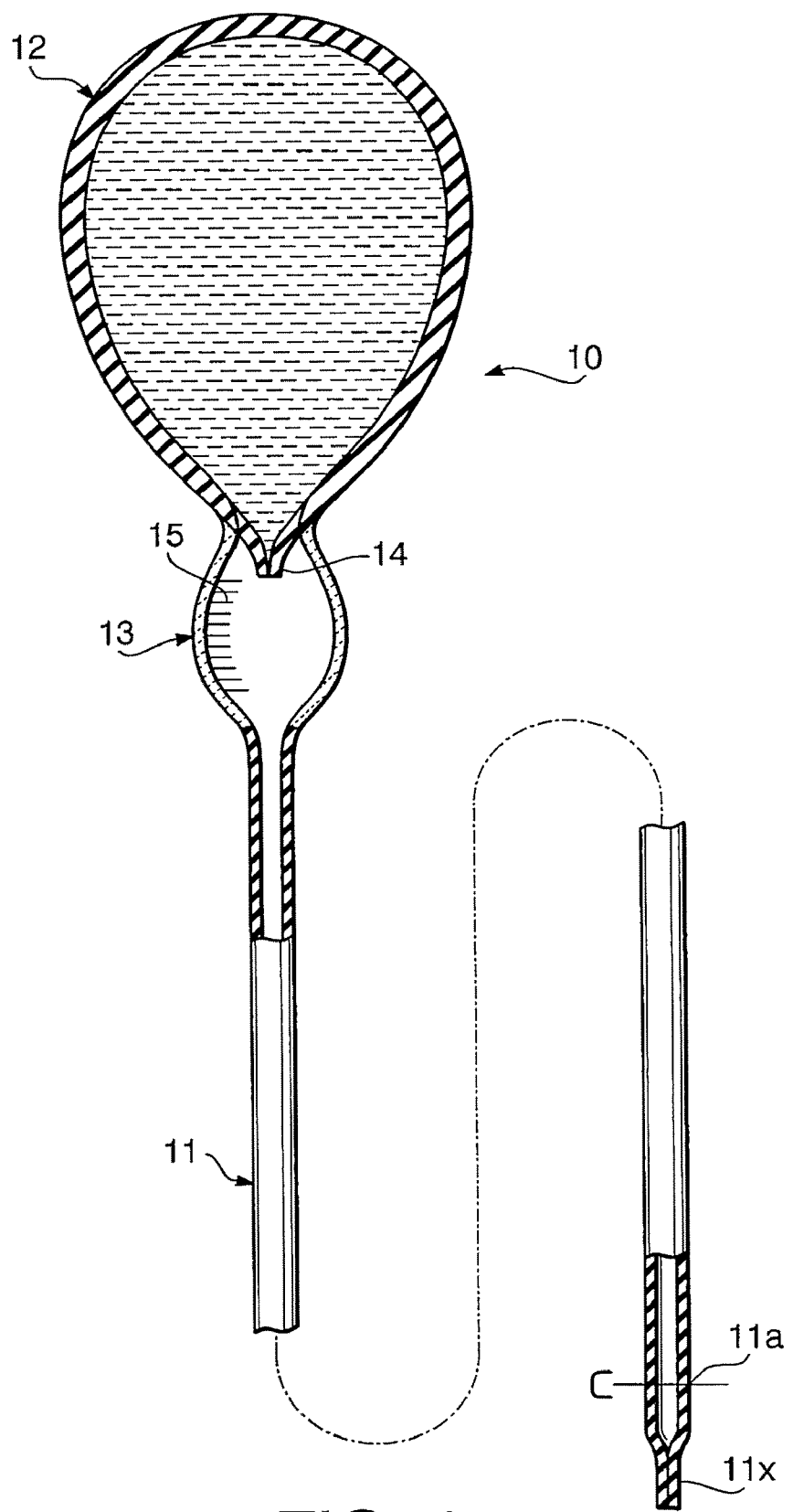
FIG. 1 is a cross-sectional view showing an entire configuration of a liquid spray tool for an endoscope according to a first embodiment of the present invention.

FIG. 1 shows a whole configuration of a liquid spray tool 10 according to a first embodiment of the present invention. The liquid storage pouch 12 is formed in a pouched shape from resilient material such as silicon rubber material. In addition, all portions of the liquid storage pouch 12, except a one-way valve provided at a leading edge, are completely sealed. When the liquid storage pouch 12 is filled with solution such as fluorescent dye solution, it is desired that the liquid storage pouch 12 is formed from opaque material to prevent deterioration of the dye solution.

The liquid measuring pouch 13 is formed smaller than the liquid storage pouch 12 in volume in a shape of a barrel with a bulging middle portion from resilient material such as the same silicon rubber as the liquid storage pouch 12. Further, the liquid measuring pouch 13 is arranged to connect the rear end of the flexible tube 11 with a distal end of the liquid storage pouch 12.

The liquid measuring pouch 13 is formed from transparent material such that a liquid level of the solution pooled therein can visually be recognized. Further, the liquid measuring pouch 13 is marked with a scale 15 for measuring the amount of the solution pooled therein.

The one-way valve 14 provided at the leading edge of the liquid storage pouch 12, for example, is formed as a slit with the distal end of the liquid storage pouch 12 being narrowed and closed, and is protruded into a rear end of the liquid measuring pouch 13. Further, the one-way valve 14 is configured so that the solution can be conveyed from an inside of the liquid storage pouch 12 to an inside of the liquid measuring pouch 13 while the solution cannot be conveyed from the inside of the liquid measuring pouch 13 to the inside of the liquid storage pouch 12. It is noted that any configuration of one-way valve having the same function as that of the aforementioned one-way valve 14 may be arranged.

The flexible tube 11, for example, is of an external diameter of 2-3 mm and a wall thickness of 0.5-0.8 mm. Additionally, the flexible tube 11 is desired to be formed from the same material as the liquid storage pouch 12 and liquid measuring pouch 13 (in this case, the silicon rubber) in view of easiness in manufacturing.

It is noted that, when stronger resiliency is required for the flexible tube 11, the flexible tube 11 may be formed, for example, using a silicon resin tube or fluorocarbon resin tube of a stiffness higher than the silicon rubber tube. In addition, the rear end of the flexible tube 11 may be connected integrally with the distal end of the liquid measuring pouch 13 by welding.

A leading edge portion 11x of the flexible tube 11, for example, is squashed and hot-welded to be sealed. Consequently, all of outer surface portions of the liquid spray tool 10 are sealed against the outside.

Accordingly, the flexible tube 11 has to be cut in a position C close to the distal end thereof to be opened before use. The cut portion becomes the distal end 11a of the flexible tube 11 in use. However, if the sealing of the leading edge 11x of the flexible tube 11 is attained by adhesion of the leading edge 11x, the flexible tube 11 can be opened without being cut.

When using the liquid spray tool 10 configured as above in the embodiment, as shown in FIG. 4, the flexible tube 11 is inserted through the treatment tool insertion channel 3 of the endoscope, and the distal end 11a of the flexible tube 11 is directed toward a target portion in a human body.

Figure 2:
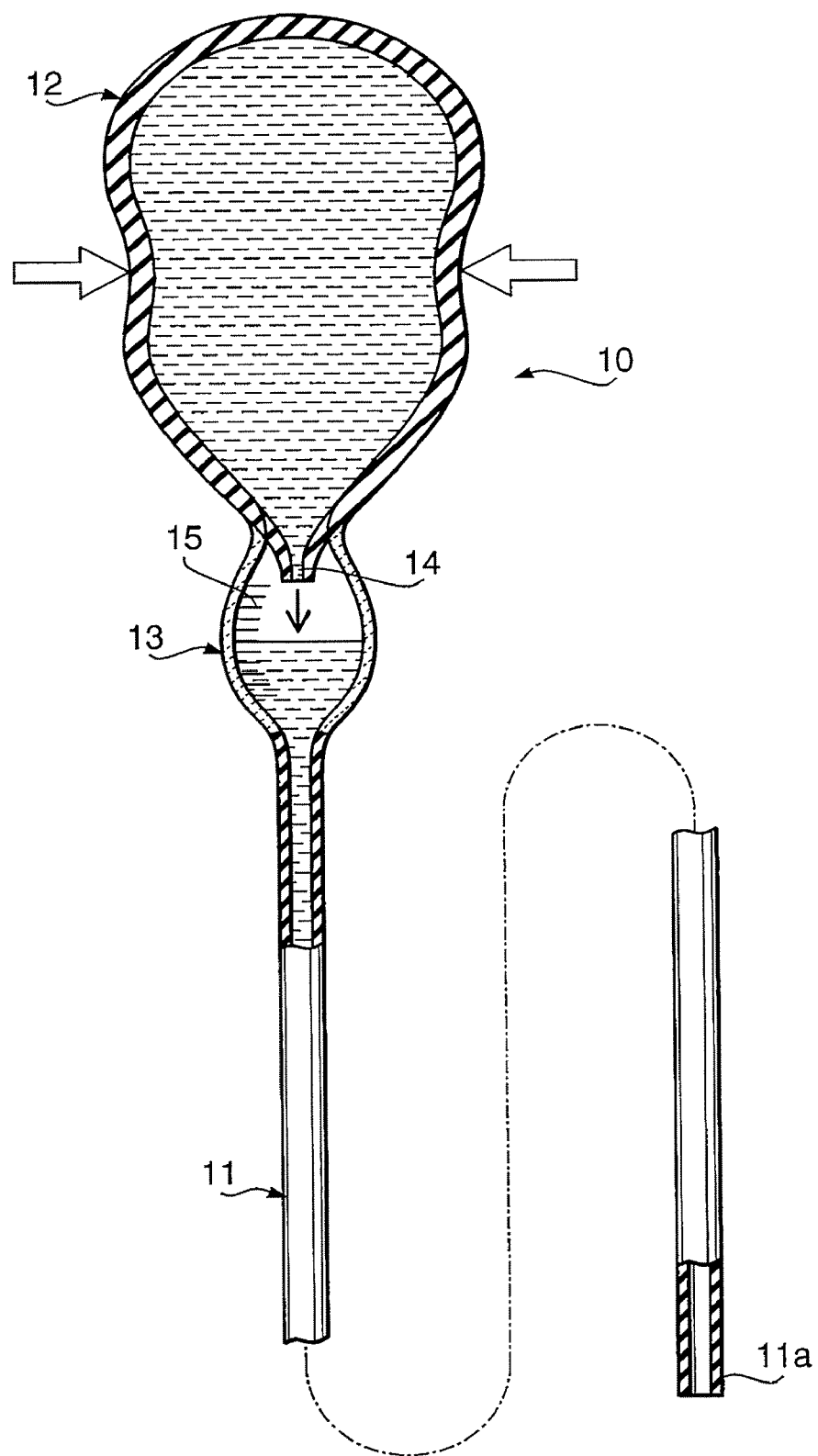
FIG. 2 is a cross-sectional view showing an operation of the liquid spray tool for the endoscope according to the first embodiment of the present invention.
Figure 3:
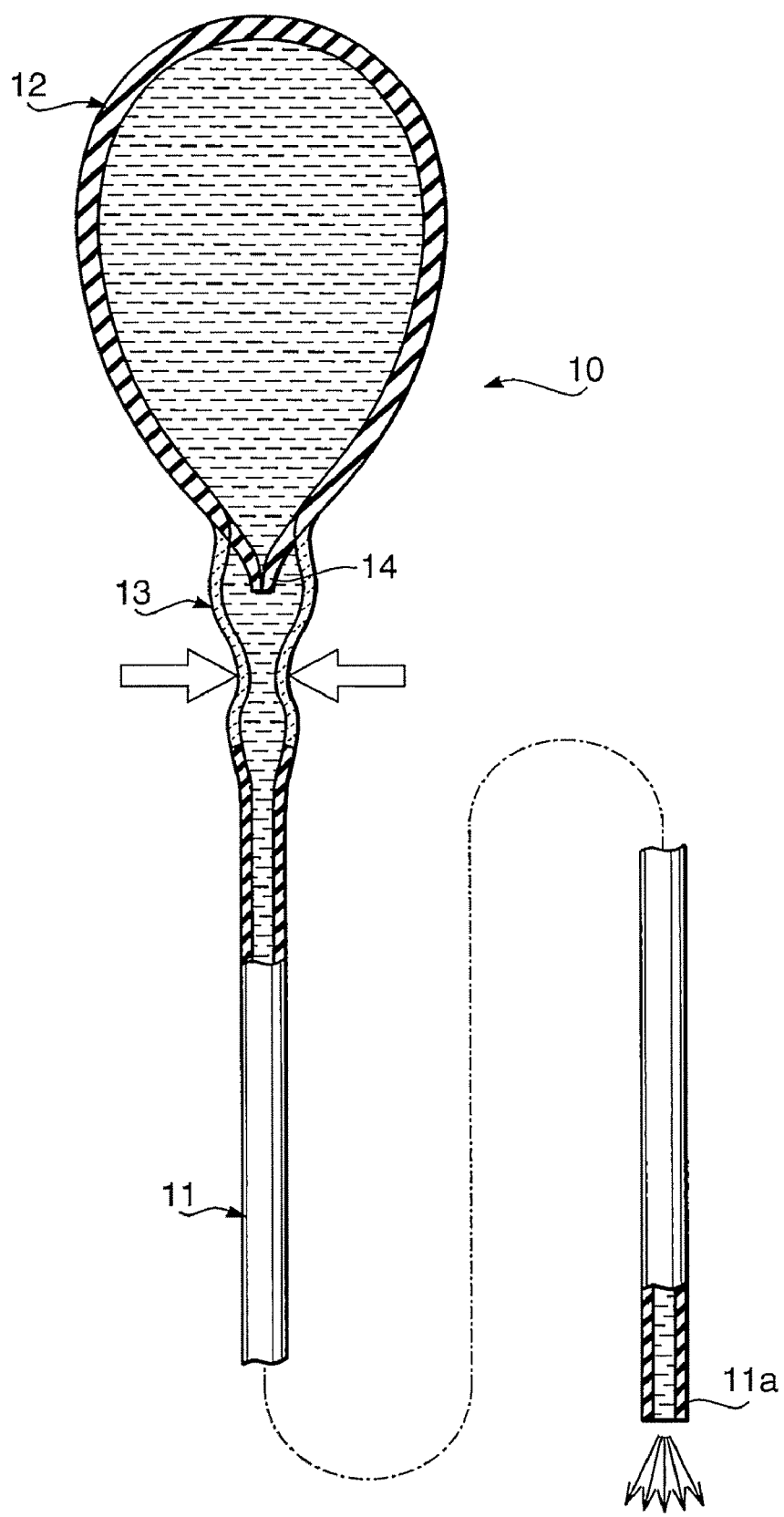
FIG. 3 is a cross-sectional view showing an operation of the liquid spray tool for the endoscope according to the first embodiment of the present invention.

Then, as shown in FIG. 2, the solution is pushed out of the liquid storage pouch 12 into the liquid measuring pouch 13 with an operation of pressing the liquid storage pouch 12 being carried out by hand. After an appropriate amount of solution has been confirmed to be pooled in the liquid measuring pouch 12 with the scale, as shown in FIG. 3, with an operation of pressing the liquid measuring pouch 13 being carried out by hand, the solution is sprayed into the human body from the distal end 11a of the flexible tube 11.

Thus, by the liquid spray tool 10 according to the present invention, it is possible to repeatedly perform a similar operation of spraying the solution as required. In addition, since all of the outer surface portions, except the distal end 11a of the flexible tube 11, are sealed, liquid leak is completely prevented.

Figure 5:
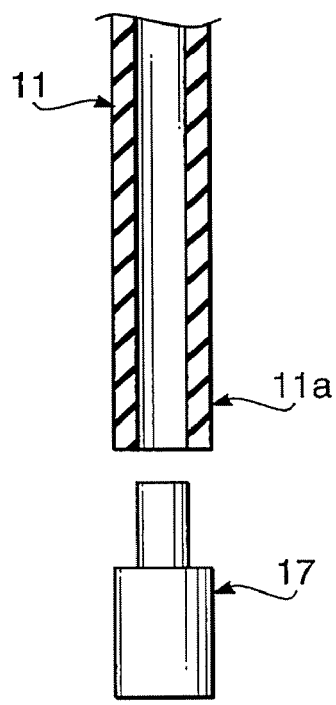
FIG. 5 is a cross-sectional view of a distal end portion of a liquid spray tool for the endoscope according to a second embodiment of the present invention.

It is noted that the present invention is not limited to the aforementioned embodiment. For example, as shown in FIG. 5 (a second embodiment), the liquid spray tool may be configured such that a detachable stopple 17 is inserted the distal end 11a of the flexible tube 11, instead of sealing the leading edge of the flexible tube 11.

Figure 6:
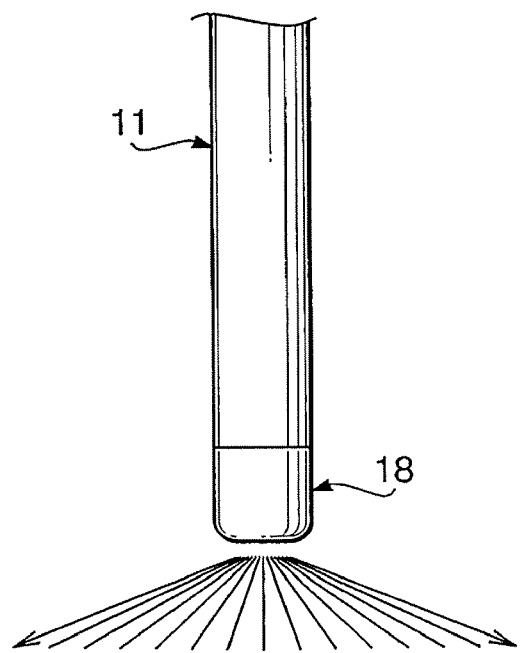
FIG. 6 is an external view of the distal end portion of a liquid spray tool for the endoscope according to a third embodiment of the present invention.

In addition, as shown in FIG. 6 (a third embodiment), the liquid spray tool may be configured such that, with a spray pipe sleeve 18 being attached to the distal end portion of the flexible tube 11 as described in Japanese Patent Provisional Publication No. 2001-104489, the solution can be sprayed to a wide ranging area in the human body as mist.

Figure 7:
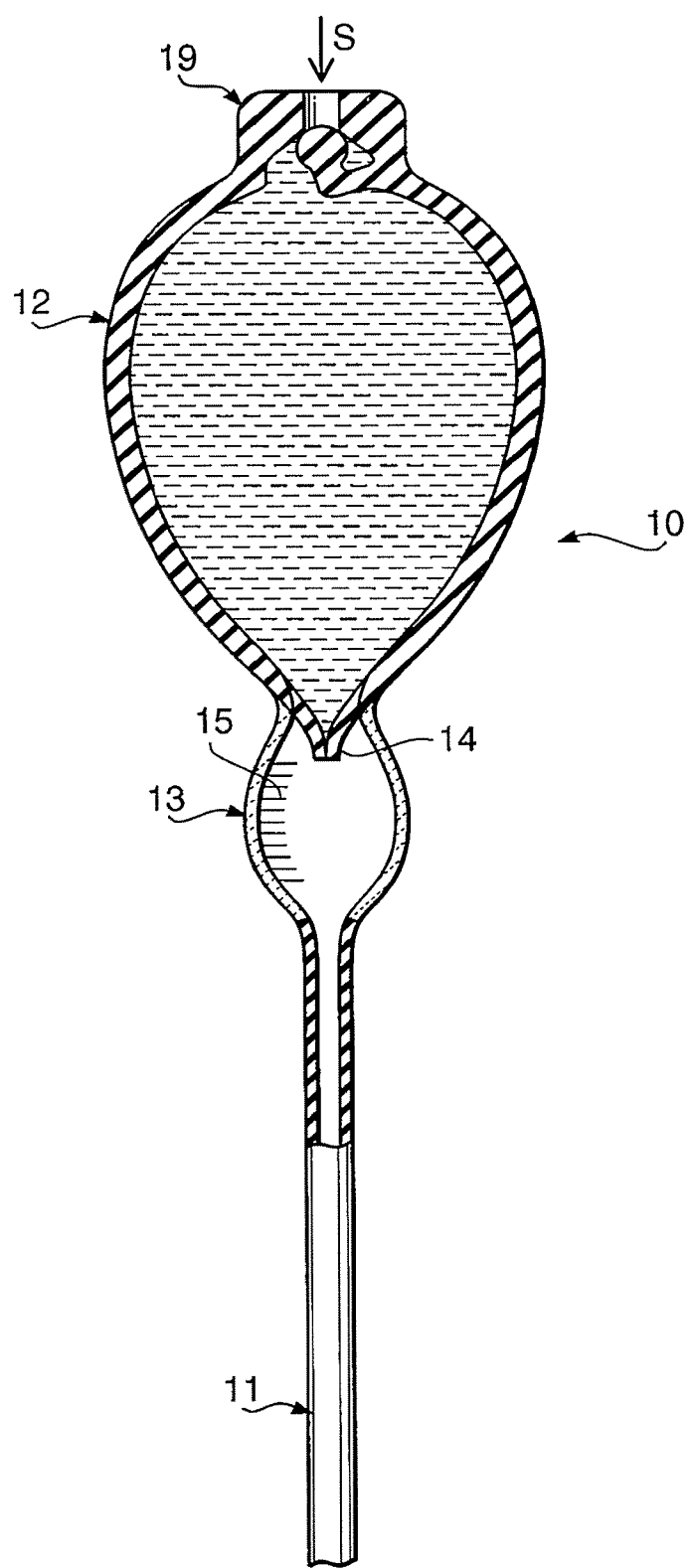
FIG. 7 is a cross-sectional view of a rear end portion of a liquid spray tool for the endoscope according to a fourth embodiment of the present invention.

In addition, as shown in FIG. 7 (a fourth embodiment), in the vicinity of a rear end of the liquid storage pouch 12, there may be provided a one-way valve 19 configured such that air can pass therethrough into the liquid storage pouch 12 from an outside of the pouch 12 as indicated by an arrow S. According to the liquid spray tool configured as above, the air corresponding to an amount of the solution being conveyed into the liquid measuring pouch 13 from the liquid storage pouch 12 is inhaled into the liquid storage pouch 12 from the outside.

The one-way valve 19 in the fourth embodiment is configured such that a spherical body is elastically pressed to an inner opening of an opening that opens toward an outside of the liquid storage pouch 12. However, other configurations may be possible.

The present disclosure relates to the subject matter contained in Japanese Patent Application No. P2005-364521, filed on Dec. 19, 2005, which is expressly incorporated herein by reference in its entirety.

What is claimed is:

1. A liquid spray tool for an endoscope configured to spray solution to in vivo tissue, comprising:
   a flexible tube to be inserted into and extracted from a treatment tool insertion channel of the endoscope;

a liquid storage pouch configured to pool the solution to be conveyed into the flexible tube therein;

a liquid measuring pouch for measuring an amount of the solution to be conveyed into the flexible tube, the liquid measuring pouch being arranged between a rear end of the flexible tube and a distal end of the liquid storage pouch; and a first one-way valve arranged between the liquid storage pouch and the liquid measuring pouch, the first one-way valve being configured to allow the solution to pass theretrough from an inside of the liquid storage pouch to an inside of the liquid measuring pouch, and to prevent the solution from passing theretrough from the inside of the liquid measuring pouch to the inside of the liquid storage pouch.

2. The liquid spray tool according to claim 1,
wherein the liquid measuring pouch is configured to have a volume smaller than that of the liquid storage pouch.

3. The liquid spray tool according to claim 1,
wherein the liquid storage pouch is formed from opaque material.

4. The liquid spray tool according to claim 1,
wherein the first one-way valve is formed with the distal end of the liquid storage pouch being narrowed.

5. The liquid spray tool according to claim 1,
wherein the liquid measuring pouch includes a scale for measuring an amount of the solution pooled therein.

6. The liquid spray tool according to claim 1,
wherein all of outer surface portions thereof, including a distal end of the flexible tube, are sealed against an outside of the liquid spray tool.

7. The liquid spray tool according to claim 6,
wherein the distal end of the flexible tube is sealed by welding.

8. The liquid spray tool according to claim 1, further comprising a stopple for sealing a distal end of the flexible tube.

9. The liquid spray tool according to claim 1, further comprising a second one-way valve configured to allow air to pass therethrough from an outside to an inside of the liquid storage pouch into the liquid storage pouch, and to prevent the solution from passing therethrough from the inside to the outside of the liquid storage pouch.

10. The liquid spray tool according to claim 1,
wherein the liquid storage pouch is formed from resilient material.

11. The liquid spray tool according to claim 10,
wherein the liquid storage pouch is formed from silicon rubber.

12. The liquid spray tool according to claim 1,
wherein the liquid measuring pouch is formed from transparent resilient material.

13. The liquid spray tool according to claim 12,
wherein the liquid measuring pouch is formed from silicon rubber.

14. The liquid spray tool according to claim 1,
wherein the flexible tube is formed from the same material as at least one of the liquid storage pouch and liquid measuring pouch.

15. The liquid spray tool according to claim 1,
wherein the flexible tube is formed from silicon rubber.

16. The liquid spray tool according to claim 1,
wherein the flexible tube is formed from material of a stiffness higher than silicon rubber.

17. The liquid spray tool according to claim 16,
wherein the flexible tube is formed from silicon resin.

18. The liquid spray tool according to claim 16,
wherein the flexible tube is formed from fluorocarbon resin.

* * * * *